US006525145B2

(12) United States Patent
Gevaert et al.

(10) Patent No.: US 6,525,145 B2
(45) Date of Patent: Feb. 25, 2003

(54) POLYLACTIDE/DEXTRAN GRAFT CO-POLYMERS FOR BIOMATERIAL AND TISSUE ENGINEERING APPLICATIONS

(75) Inventors: Matthew R. Gevaert, Central, SC (US); Stephen Massia, Apache Junction, AZ (US)

(73) Assignee: Clemson University, Clemson, SC (US)

( * ) Notice: Subject to any disclaimer, the term of this patent is extended or adjusted under 35 U.S.C. 154(b) by 51 days.

(21) Appl. No.: 09/857,157

(22) PCT Filed: Apr. 18, 2001

(86) PCT No.: PCT/US01/12604

§ 371 (c)(1),
(2), (4) Date: May 31, 2001

(87) PCT Pub. No.: WO01/79315

PCT Pub. Date: Oct. 25, 2001

(65) Prior Publication Data

US 2002/0161136 A1 Oct. 31, 2002

Related U.S. Application Data

(60) Provisional application No. 60/197,697, filed on Apr. 18, 2000.

(51) Int. Cl.[7] .......................... C08F 251/00; C07H 1/00; A01N 43/04; A61K 9/14

(52) U.S. Cl. .......................... 525/450; 525/78; 525/79; 525/418; 536/4.1; 536/123.1; 536/124; 514/54; 514/58; 424/426; 424/486; 424/458

(58) Field of Search ............................ 525/450, 78, 79, 525/418; 536/4.1, 123.1, 124; 514/54, 58; 424/426, 486, 488

(56) References Cited

U.S. PATENT DOCUMENTS

| 4,741,337 A | 5/1988 | Smith et al. |
| 5,041,292 A | 8/1991 | Feijen |
| 5,514,379 A | 5/1996 | Weissleder et al. |

OTHER PUBLICATIONS

US/ISA, International Search Report 3 pages, Aug. 2, 2001; US.

Primary Examiner—Duc Truong
(74) Attorney, Agent, or Firm—Dority & Manning, PA

(57) ABSTRACT

A biocompatible, biodegradable, copolymer is prepared from cross-linking a polylactic acid with a polysaccharide such as dextran. The resulting copolymer is a biodegradable hydrogel or solid having both hydrophobic and hydrophilic properties and provides for a mechanism in which biologically active agents may be covalently bonded to the dextran prior to incorporation of the dextran into a copolymer, and the subsequent release of the biologically active agents as the copolymer degrades.

14 Claims, 2 Drawing Sheets

FTIR SPECTRUM OF 95/5 COPOLYMER

POLYLACTIDE/DEXTRAN GRAFT CO-POLYMERS FOR BIOMATERIAL AND TISSUE ENGINEERING APPLICATIONS

RELATED APPLICATION

This application claims the benefit of U.S. Application No. 60/197,697 filed Apr. 18, 2000 and which is incorporated herein by reference.

FIELD OF THE INVENTION

The present invention relates to a biodegradable copolymer useful in biomedical applications, including use as a tissue filler, a tissue adhesive, a bio-medical scaffold, and for the controlled delivery of pharmacological agents.

BACKGROUND OF THE INVENTION

Biodegradable polymers are well known within the art as carriers for biologically active materials. Such biologically active materials may include therapeutic agents such as drugs, antibiotics, enzymes, and hormones. Further, polymers which form hydrogels can be used as carriers for cell suspensions and to increase the functional life of a carried material or agent. Copolymers can have an extensive range of permeability, pore sizes, and degradation rates which may be tailored for individual applications involving surgery, medical diagnosis, treatment, and research needs. Biodegradable synthetic polymers have evolved extensively since the first polylactic acid polymer was reported by Kulkierni et al 1966 "Polylactic Acid for Surgical Implants," *ARC Surg* 93:839. Polyesters of lactic acid and glycolic acid have been widely used as biodegradable materials for drug delivery systems as set forth in U.S. Pat. No. 4,741,337 to Smith et al which is incorporated herein by reference. Frequently, the matrix of biodegradable polymers is hydrophobic in nature. Containment within such a matrix may result in certain enzymes and hydrophilic materials being present in an inactive conformation or undergoing an irreversible denaturation as a result of contact with solvents used in dispersing the carrier molecules within the polymer. While it has been suggested that rapidly degrading polymers may be used for short-term drug release, such use raises concerns of complications from acidic degradation by-products. Further, many biodegradable synthetic polymers require processing using organic solvents which present additional potential hazards. Accordingly, there remains room for improvement and variation within the art of synthetic biodegradable polymers.

SUMMARY OF THE INVENTION

Disclosed herein is a biocompatible, biodegradable, copolymer containing both hydrophobic and hydrophilic macromers. The resulting copolymer has a variety of uses in vivo. The copolymer has a water-soluble component in the form of an OH-containing polysaccharide such as dextran. An additional component of the copolymer is made from a hydrophilic polymer such as polylactide. In accordance with one aspect of this invention, it has been found that the macromers may be co-polymerized to form a copolymer having new and useful properties.

It is yet another aspect of this invention to provide a copolymer comprising a mixture of a polylactic acid which is co-polymerized with dextran. In one aspect of the present invention, the dextran has, prior to incorporation into the copolymer, been covalently bonded to a therapeutic agent such as a drug, hormone, or other useful molecule. The resulting copolymers are particularly useful for controlled drug delivery especially for use with a hydrophilic material, since the water-soluble region of the polymer may enable access of water to materials which may be embedded within the polymer matrix.

In yet another aspect of the invention, it is possible to incorporate materials which are entrapped in a non-covalent manner within the copolymer. Such materials may be introduced during the polymerization stage and offer an ability to provide two different release mechanisms of one or more biologically useful additives. For instance, release of non-covalently bound materials may occur by diffusion of the material from the copolymer prior to copolymer degradation or may result from release of the copolymer matrix as the polymer degrades. The release of entrapped materials may be regulated in part by the molecular weight of the various macromers and the cross-link density.

It is yet another aspect of the invention to provide a biodegradable copolymer in which the degraded constituents result in the formation of lactic acid and a polysaccharide such as glucose.

Certain aspects of the invention are provided by a copolymer in the form of a biocompatible, biodegradable, copolymer comprising a first backbone molecule of PLA bonded via a cross-linking reaction to a second backbone molecule of dextran wherein the dextran provides multiple hydroxyl functionalities.

An additional aspect of the invention is provided by a process of delivering a therapeutic agent to a patient comprising the steps of providing a first polymer of PLA; providing a second polymer of a polysaccharide; covalently bonding at least one therapeutic agent to the second polymer; cross linking the first polymer to the second polymer, thereby forming a copolymer; introducing the copolymer to a patient; releasing within the patient the at least one therapeutic agent from the second copolymer; degrading a portion of said PLA into lactic acid; and, releasing said lactic acid from the copolymer along a hydrophilic channel of the copolymer defined by the polysaccharide, thereby, slowing the degradation rate of the remaining portion of the PLA.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus or process pathway. To avoid redundancy, detailed descriptions of much of the apparatus once described in relation to a figure is not repeated in the descriptions of subsequent figures, although such apparatus or process is labeled with the same reference numbers.

Figure 1A:
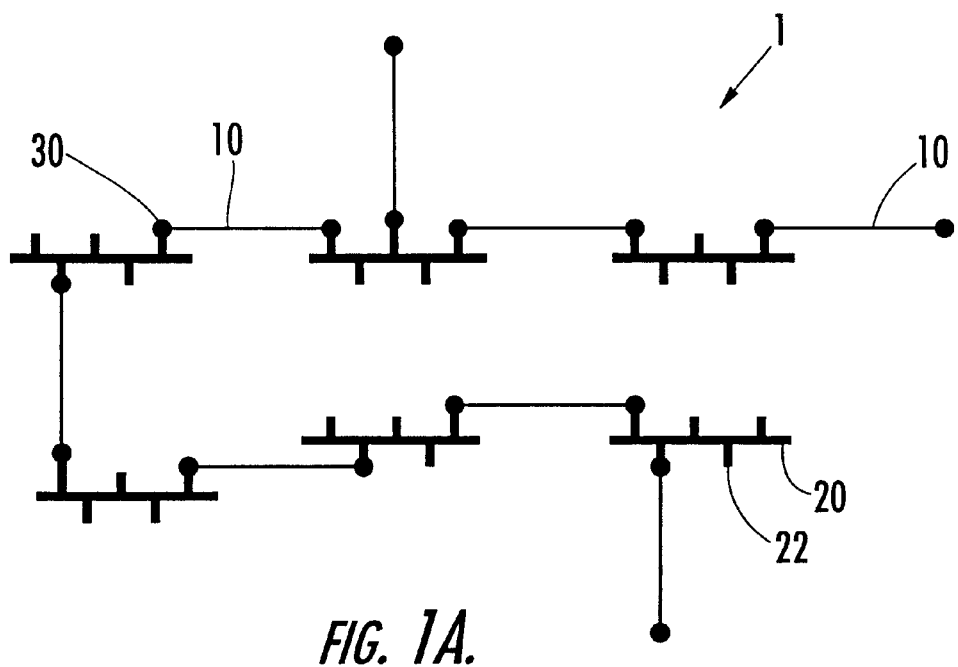
FIGS. 1A and 1B are schematic illustrations of the drawing of macromers of the present invention in which a polylactic acid is polymerized with dextran, the dextran having additional covalently attached biological agents.
Figure 1B:
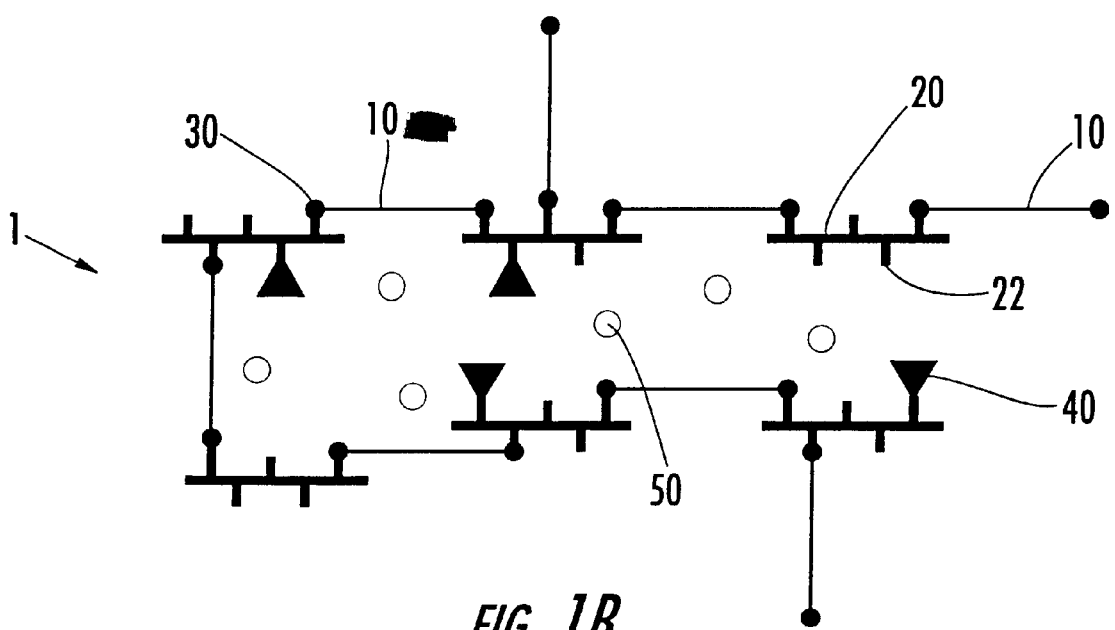

As best seen in reference to FIGS. 1A and 1B, the copolymer composition includes a first polymer backbone 10, a second polymer backbone 20, cross link 30 between the two backbones, and at least one covalently bonded, therapeutic agent 40. Actually, there may be an additional material 50 present which is non-covalently bound within the hydrogel matrix.

The copolymer composition includes a hydrophilic macromolecule 20 with multiple side functionalities 22 which are available to react and form cross-links 30 aided by a catalyst. One such macromolecule 20 includes free hydroxyl (OH) groups, for example a neutral homopolysaccharide consisting of glucose units joined predominantly by α (1–6 or 1–4) glycosidic bonds. Dextran is a water-soluble polymer which is cleaved primarily into glucose in vivo. Dextran provides the advantages of having multiple hydroxyl functionalities which may serve as potential reaction sites, as well as being biodegradable into neutral glucose units. As a hydrophilic, water-soluble macromer, the dextran may be incorporated into a copolymer to enhance stability and drug delivery applications for hydrophilic compounds. In addition, the hydrolysis rate may be altered by using dextran, which contains 1,4 glycosidic linkages which are more persistent in vivo than the 1,6 linkages found in other common biological polysaccharides.

A second component of the copolymer composition includes a hydrophobic macromolecule 10 such as polylactic acid (PLA). The reaction is catalyzed by magnesium acetate tetrahydrate which brings about the co-polymerization between the dextran and the PLA. As best seen in reference to FIG. 1B, additional molecules 40 may be covalently bonded to the polydextran 20 via the hydroxyl functionalities 22. The agent 40 may be any number of therapeutic or biologically active molecules such as antibiotics, hormones, or similar useful additives.

The resulting copolymer of PLA cross-linked with dextran is particularly useful for controlled drug delivery. The hydrophilic nature of dextran provides a water-soluble region within the polymer which enables access of water to materials which may be present within the polymer. As a result, release may occur by diffusion of the entrapped material from the polymer prior to degradation and/or by diffusion of the material from the polymer as it degrades. Deactivation of the entrapped material can be reduced by the presence of a hydrophilic environment. Further, the dextran subunits offer a number of free OH groups which are amenable to covalent bonding of various biologically active agents. As a result, the hydrogel can have incorporated therein biological agents which are covalently bonded and therefore offer different release rates as opposed to other materials which may be merely entrapped within the copolymer matrix.

The synthesis and characterization of a polylactic acid/dextran copolymer may be found in reference to a publication of the co-inventor Matthew R. Gevaert entitled "Synthesis and Characterization of a Novel Poly (lactic acid)-Dextran Co-polymer for Biomaterial Applications" which is a thesis prepared for Clemson University, Clemson, S.C., dated May, 1999 and which is incorporated herein by reference.

The relative percentage (w/w) of dextran to PLA may be varied as needed. Initial studies have used dextran loadings of 5% and less in order to facilitate available extraction and separation technologies to verify co-polymerization and for comparative purposes to 100% PLA control polymers. However, various combinations and percentages of dextran and PLA which form useful substrates may be used to advantage as described herein.

Materials used in the following example include PLA obtained from PolySciences and having a molecular weight of 50,000 g/mol. The dextran was obtained from Polysciences (#01341) and has a molecular weight range of 15,000 to 20,000. However, variations of the molecular weights of the polymers may be made and are operational within the parameters of the present invention. Magnesium acetate tetrahydrate $(CH_3CO_2)_2Mg4H_2O)$ (Aldrich) is provided as a catalyst and is typically provided in small, catalytic amounts. A general protocol is set forth below as Example 1.

EXAMPLE 1

46 ml of DMSO was used to dissolve 9.5 gm of PLA at a temperature of 130° C. 4 ml of DMSO was to dissolve 0.5 gm dextran and catalytic amount (1 mg or less) of magnesium acetate catalyst. Once the reagents are in solution, the solutions are combined and stirred in an 130° C. oil bath for 24 hours in an oxygen free, nitrogen flushed environment.

A covalently bonded co-polymer reaction product results from a transesterfication reaction as illustrated below. This type of reaction is known to be catalyzed by metal acetates or by certain weak acids and bases.

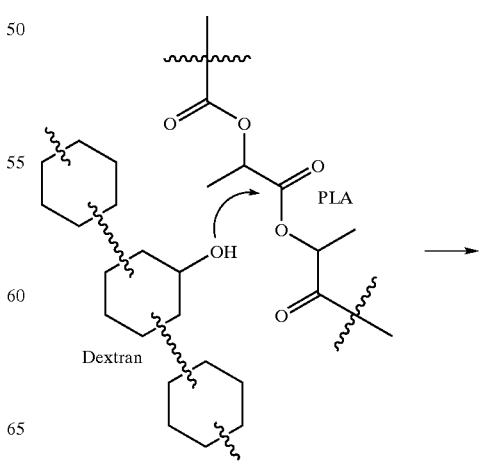

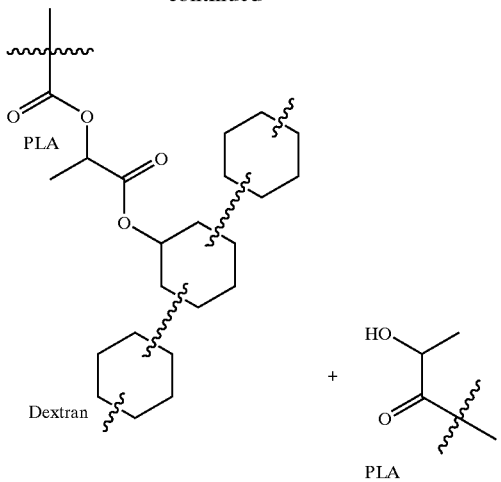

Transesterification Reaction of PLA and Dextran

Following the reaction, the co-polymerization reaction product is purified by drop-wise precipitation into a 2 liter volume of cold methanol. The resulting precipitation product is collected by conventional methods such as vacuum filtration or centrifugation. The precipitation product in the form of a light solid, is collected and dried in a 35° C. vacuum oven at 17 mm Hg overnight. Set forth in Table 1 is data from co-polymerization runs and appropriate experimental controls.

| Reaction | Mass PLA (g) | Mass Dextran (g) | Mass catalyst (mg) | Mass recovered (g) | Recovery (%) |
|---|---|---|---|---|---|
| 99/1 | 9.8975 | 0.104663 | 1.0 | 6.56824 | 65.36 |
| 98/2 | 9.79248 | 0.20425 | 1.0 | 6.86267 | 68.29 |
| 95/5 | 9.5092 | 0.50813 | 1.0 | 6.63997 | 65.97 |
| 100/0 | 9.92816 | 0 | 1.0 | 7.2962 | 73.12 |
| NoCat | 9.49460 | 0.50716 | 0 | 8.61183 | 86.10 |
| NoHeat | 9.50450 | 0.50293 | 1.0 | 9.31198 | 92.59 |

Mass of Reagents and Recovery in Main Copolymerization Reactions

Co-polymer Characterization

Figure 2:
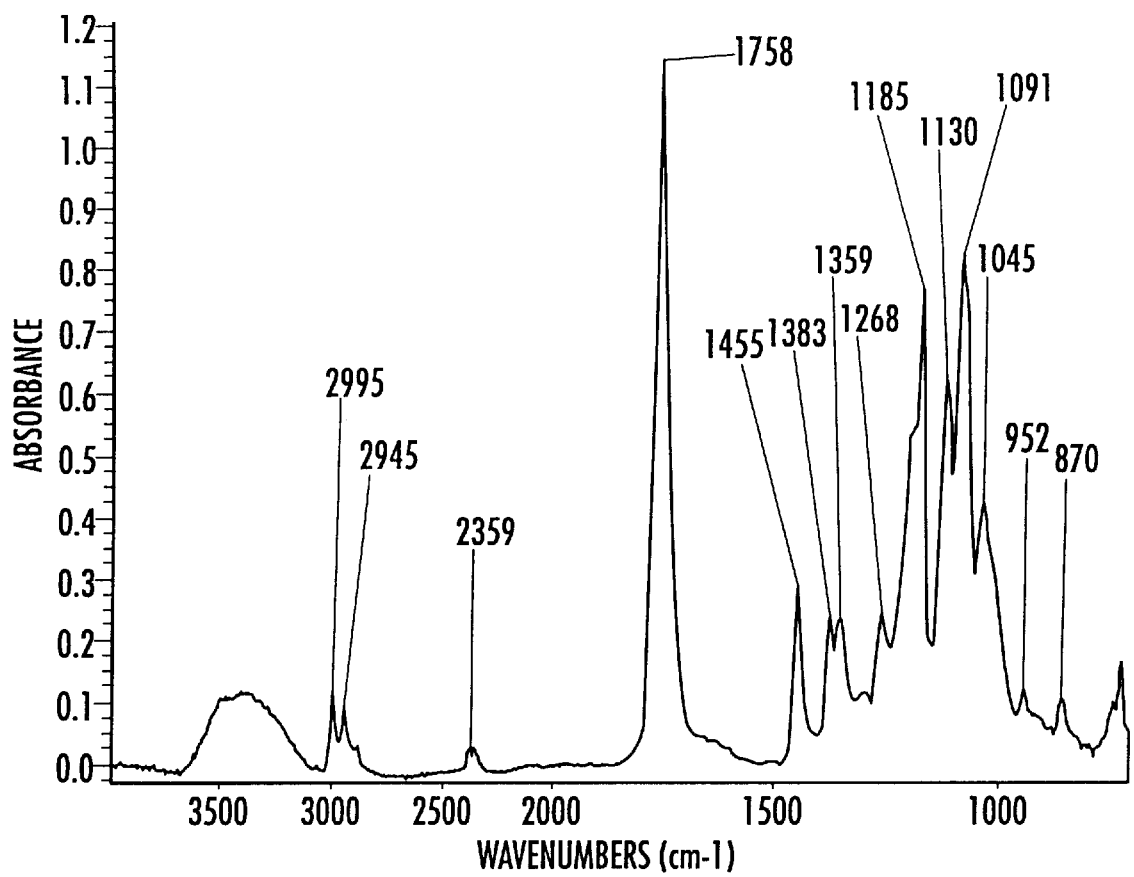
FIG. 2 is a FTR spectrum used to identify dextran in a copolymer.

Fourier transform infrared (FTIR) spectra were used to verify the presence of dextran within the co-polymer product. Set forth in FIG. 2 is a spectrum of the 95/5 co-polymer which reveals expected peaks associated with dextran which include a broad OH peak around 3360 $cm^{-1}$, a peak buried within the carbonyl peak at 1759 $cm^{-1}$, and an additional dextran peak at 1015 $cm^{-1}$ resulting in a more prominent shoulder of the expected and observed PLA peak at 1045 $cm^{-1}$. It is important to note that these dextran peaks were not present in matched controls, the dextran having been separated out during the precipitation step.

While not separately reported herein, it was noted that during liquid-liquid extractions of reaction products in which the dextran content was greater than 5% (w/w), the resulting reaction product precipitated in both aqueous and organic phases and was, thus, difficult to separate for purposes of characterization in reasonable quantities using traditional laboratory methods. This observance also helps confirm the presence of the covalently bonded co-polymers of dextran-PLA in that such a product would be expected to have both hydrophobic and hydrophilic components and would exhibit a detergent-like separation behavior. It was, indeed, observed that separation via organic and aqueous phase separation was difficult to do with dextran percentages greater than 5%.

The data set forth above indicates that formation of a covalently bonded co-polymer of dextran and PLA does occur. Such a co-polymer, offers numerous advantages and new opportunities for bio-medical applications. For instance, the inclusion of dextran, as well as other polysaccharides having similar covalent binding capabilities with PLA, provides a matrix component which is readily biodegradable in vivo into non-toxic sugars. For this reason, inclusion of the dextran into a polymer or biogel avoids toxicity concerns.

Additionally, dextran, chitosan, cellulose, and similar polysaccharides which posseses hydroxyl groups along the polymer chain permit biologically active molecules to be covalently bonded to the polymer. The covalent bonding of an antibiotic or other pharmacologically active material onto the dextran polymer, prior to gel formation, offers an alternative delivery method for the active material. This process is particularly well suited for hydrophilic agents since the dextran polymer to which the agent is attached is also hydrophilic and can maintain the agent in an aqueous micro environment following formation of the co-polymer and subsequent hydration in an aqueous macroenvironment. Additionally, the co-polymer of the present invention offers an additional control mechanism for timed release/breakdown of the biogel or polymer and the agents attached to or contained therein. For instance, hydrolysis of the dextran molecule is one such release mechanism. Or, aqueous pathways provided by hydrophilic regions may facilitate the release of acidic PLA degradation products and avoid auto-acceleration of the PLA degradation process. Therefore, the hydrolysis rate may be controlled by the amount of dextran incorporated into the co-polymer. In addition, the hydrolysis rate may be altered by using dextran, which contains 1,4 glycosidic linkages which are more persistent in vivo than the 1,6 linkages found in other common biological polysaccharides.

The relative amounts of dextran which may be incorporated into or with PLA in a copolymer may be varied over a wide range. For example, dextran or other polysaccharides may be present in the range of about 5% to about 30% (w/w) or greater. Such ranges offer the ability to provide co-polymers having a variety of physical properties. Such properties include solid or gel properties, variations in hydrolysis rates, and a wide range of the number of available binding sites available for covalent interaction with other biological and chemical agents.

It is also possible to covalently link to the dextran or other polysaccharide polymer more than one therapeutic agent. For instance, a first therapeutic agent such as a hormone may be present along with a second therapeutic agent such as an antibiotic. The resulting copolymer could be used as a tissue filler where the hormone may be used to suppress inflammation or promote a regeneration of tissue while the antibiotic provides for a localized activity of an antibiotic. In addition, a non-covalently bound therapeutic agent may be entrapped within matrix in combination with one or more covalently bound therapeutic agents. The entrapped material may be released by simple diffusion and/or in response to natural degradation and hydrolysis of the accompanying copolymer.

The resulting copolymer is also useful as a tissue filler. As a tissue filler, the hydrogel or resulting copolymer biosolid can provide a scaffold or template upon which cells can grow in an invasive and penetrating manner. As the dextran degrades over time, the growing tissue can supplant the degraded polymer components. The low toxicity and naturally metabolized constituents which make up both the dextran and PLA components of the copolymer lends itself well for use in such applications. As is readily appreciated by one having ordinary skill in the art, the PLA by-product of lactic acid is naturally metabolized in most higher animals. Toxicity of lactic acid becomes a concern only in large concentrations which may be readily avoided in applications of the present copolymer Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. A biocompatible, biodegradable, copolymer comprising a first backbone molecule of PLA bonded via a cross-linking reaction to a second backbone molecule of dextran wherein said dextran provides multiple hydroxyl functionalities.

2. The copolymer according to claim 1 wherein the second backbone molecule of dextran further comprises a covalently bound therapeutic agent.

3. The copolymer according to claim 2 wherein said therapeutic agent is selected from the group consisting of a pharmacological agent, a hormone, a biologically active molecule, an antibiotic, or a combination thereof.

4. The copolymer according to claim 1 wherein the copolymer further defines a matrix containing therein a therapeutic agent physically entrained within said matrix.

5. The copolymer according to claim 2 wherein the copolymer further defines a matrix containing therein a therapeutic agent physically entrained within said matrix.

6. A process of delivering a therapeutic agent to a patient comprising:
   providing a first polymer of PLA;
   providing a second polymer of a polysaccharide;
   covalently bonding at least one therapeutic agent to the second polymer;
   cross linking the first polymer to the second polymer, thereby forming a copolymer;
   introducing the copolymer to a patient; and,
   releasing within said patient the at least one therapeutic agent from the second copolymer.

7. The process according to claim 6 wherein said polysaccharide is dextran.

8. The process according to claim 6 comprising the additional step of hydrolyzing said second polymer.

9. The process according to claim 7 comprising the additional step of hydrolyzing said dextran to glucose.

10. The process according to claim 7 wherein said dextran contains 1, 4, glycosidic linkages.

11. The process according to claim 6 comprising the additional steps of:
    degrading a portion of said PLA into lactic acid; and,
    releasing said lactic acid from said copolymer along a hydrophilic channel of the copolymer defined by the polysaccharide, thereby, slowing a degradation rate of a remaining portion of said PLA.

12. The process according to claim 6 additionally comprising the steps of introducing a second therapeutic agent during the cross linking step, thereby providing a therapeutic agent entrapped within a matrix defined by the formed copolymer.

13. A biocompatible, biodegradable, copolymer tissue support consisting essentially of a first backbone molecule of PLA cross linked to a second backbone molecule of dextran.

14. The copolymer according to claim 1 wherein said second backbone molecule of dextran is present in a range of about 5% to about 30% by weight.

* * * * *